(12) United States Patent
Williams et al.

(10) Patent No.: US 8,362,430 B1
(45) Date of Patent: Jan. 29, 2013

(54) METHOD FOR LARGE AND RAPID TERAHERTZ IMAGING

(75) Inventors: Gwyn P. Williams, Yorktown, VA (US); George R. Neil, Williamsburg, VA (US)

(73) Assignee: Jefferson Science Assosiates, LLC, Newport News, VA (US)

( * ) Notice: Subject to any disclaimer, the term of this patent is extended or adjusted under 35 U.S.C. 154(b) by 628 days.

(21) Appl. No.: 11/899,292

(22) Filed: Sep. 5, 2007

(51) Int. Cl.
*G01J 5/02* (2006.01)
(52) U.S. Cl. .............. 250/341.1; 250/338.1; 250/339.06
(58) Field of Classification Search ............... 250/341.1, 250/341.8, 338.1, 339.06
See application file for complete search history.

(56) References Cited

U.S. PATENT DOCUMENTS

| | | | |
|---|---|---|---|
| 5,939,721 A * | 8/1999 | Jacobsen et al. ............... | 250/330 |
| 6,714,346 B1 * | 3/2004 | Neil et al. ..................... | 359/346 |
| 6,844,688 B1 * | 1/2005 | Williams et al. ............... | 315/505 |
| 2006/0038168 A1 * | 2/2006 | Estes et al. ..................... | 257/25 |
| 2007/0267574 A1 * | 11/2007 | Krug ........................... | 250/341.1 |

OTHER PUBLICATIONS

Stuart D. Jackson, Alex Sabella, Alex Hemming, Shayne Bennetts, and David G. Lancaster, "High-power 83 W holmium-doped silica fiber laser operating with high beam quality," Opt. Lett. 32, 241-243 (2007).*

* cited by examiner

*Primary Examiner* — David Porta
*Assistant Examiner* — Jessica L Eley

(57) ABSTRACT

A method of large-scale active THz imaging using a combination of a compact high power THz source (>1 watt), an optional optical system, and a camera for the detection of reflected or transmitted THz radiation, without the need for the burdensome power source or detector cooling systems required by similar prior art such devices. With such a system, one is able to image, for example, a whole person in seconds or less, whereas at present, using low power sources and scanning techniques, it takes several minutes or even hours to image even a 1 cm×1 cm area of skin.

5 Claims, 2 Drawing Sheets

METHOD FOR LARGE AND RAPID TERAHERTZ IMAGING

The United States of America may have certain rights to this invention under Management and Operating Contract DE-AC05-06OR23177 from the United States Department of Energy.

FIELD OF THE INVENTION

The present invention relates to methods for the acquisition of large terahertz images and more particularly to the acquisition of such images at real time/video speeds.

BACKGROUND OF THE INVENTION

Terahertz (THz) light lies in the frequency range between photonics and electronics and holds enormous promise for unique non-ionizing imaging applications, as well as in novel linear and non-linear device development. For example, THz imaging holds promise in the detection of epithelial cancer, in security applications such as detection of explosives and hidden weapons, in the analysis of bio-chemical threats, in quality control etc., among many other useful applications.

Prior art systems have been used to actively image objects in the THz region but, in general, the area imaged was quite small (1 $cm^2$ or less) so that the sample or light source had to be raster scanned or the time required to integrate sufficient signal for detection was increased to many seconds, minutes or even hours.

Most efforts to develop useable imaging systems have focused on the development of ever more sensitive imaging system detectors that can detect THz radiation of very low power, on the order of very small fractions of a watt, i.e. µWatts. This has been primarily due to the need for very powerful THz light generators that require very sophisticated and cumbersome cooling devices to generate even moderately high power THz radiation (on the order of 1 watt) or detectors that were similarly encumbered by the need for burdensome cooling systems to obtain THz images from such relatively higher wattage THz light generators. Even with such highly sophisticated prior art systems, the acquisition of even "still" THz images required from minutes to hours. Hence, the development of "real time" THz based imaging systems such as those that could acquire video images or provide useful detectors for a variety of security applications that require instantaneous image acquisition is and has been stymied.

Accordingly, there remains a need for THz imaging systems that are capable of instantaneously acquiring THz images with all of the attendant benefits that THz imaging can provide such as the detection of plastic weapons in security screening, drug detection in certain epidermal medical and postal inspection applications, food inspection systems, etc.

OBJECT OF THE INVENTION

It is therefore an object of the present invention to provide a THz light imaging system that is capable of the instant acquisition of THz images without the need for either: 1) high power THz light sources that require sophisticated and burdensome cooling systems; or 2) highly sophisticated THz light sensors that are capable of detecting very low power THz light.

SUMMARY OF THE INVENTION

According to the present invention there is provided a method of large-scale active THz imaging using a combination of a compact high power THz source (>1 watt), an optional optical system, and a camera for the detection of reflected or transmitted THz radiation, without the need for the burdensome power source or detector cooling systems required by similar prior art such devices. With such a system, one is able to image, for example, a whole person in seconds or less, whereas at present, using low power sources and scanning techniques, it takes several minutes or even hours to image even a 1 cm×1 cm area of skin.

DETAILED DESCRIPTION

Figure 1:
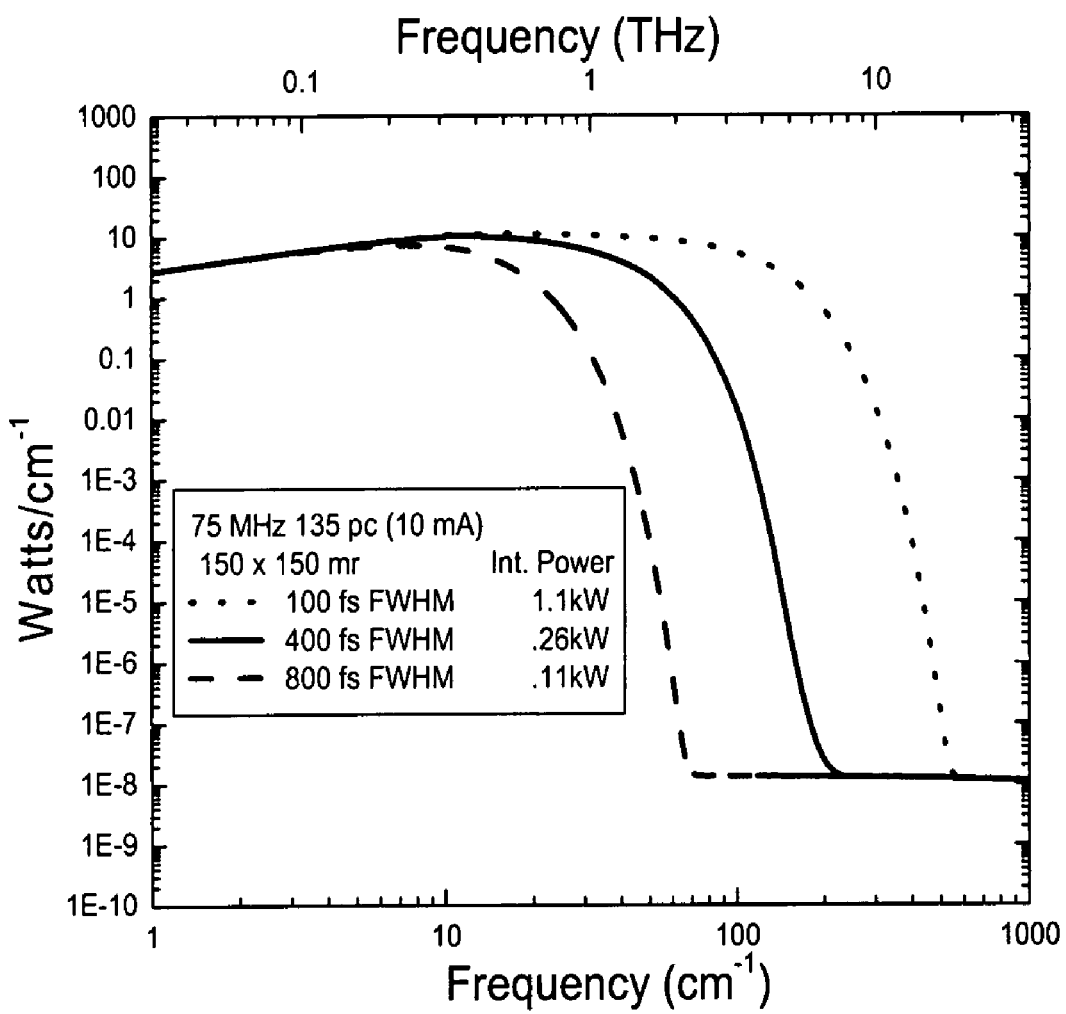
FIG. 1 is a graph of THz radiation output of this source as a function of frequency.

The developments described in U.S. Pat. No. 6,714,346 "Apparatus for THz Radiation Enhancement" and U.S. Pat. No. 6,844,688, "Multiwatt THz Generation" to Williams and Neil, which are incorporated herein by reference in their entireties, demonstrated that many watts of THz light can be produced from short electron bunches in an electron accelerator with a high charge per bunch and a relatively high repetition rate. THz radiation produced in this manner has several features which make it particularly advantageous for use in imaging: it is broadband or tunable in frequency with output wavelengths as short as the electron bunch length, on the order of picoseconds; it is produced in a narrow beam on the order of 1/gamma wide where gamma is the electrons' relativistic factor; and it can be produced at high average power, on the order of 10,000 times higher than the next most powerful broadband source. The method described in these patents comprises the use of a compact high power (greater than 1 watt) THz light source comprising: a mechanism for introducing THz radiation in the form of a beam of photon pulses comprised of a series of photon bunches from bunches of relativistic electrons In conjunction with a relatively simple THz camera, these special features make feasible imaging of large objects in a manner which is not possible using other Terahertz sources. In particular the combination of the small beam divergence and the higher power allow one to illuminate an object of large size, 1 $m^2$ or more, with sufficient power that it will still produce enough scattered or transmitted THz light intensity to be detectable at very high rates above background radiation and thermal or other types of noise.

The present invention includes the detection of either the power or the electric field produced by reflected/transmitted THz radiation, or both. Measurements of the electric field can be used to enhance the sensitivity of detection. Such coherent detection is rendered possible by utilizing light pulses synchronously derived either from an accelerator, from a drive laser, an FEL or synchrotron light as described in U.S. Pat. No. 6,714,346; or, using lock-in amplifiers which synchronously integrate the detected pulses at the electron beam pulse frequency. Another method involves utilizing part of the emitted wavefront as a reference for the other. Utilizing the broadband nature of the THz illumination means that hyperspectral techniques can be utilized to provide bio-medical, chemical or morphological information about the object under investigation. Moreover phase sensitive detection can be utilized to uncover these features in three dimensions provided the material is not excessively absorptive or dispersive of the THz radiation. It is clear that such a source can be extraordinarily versatile.

Measurements of the power can be performed thermally using bolometric or pyrometric detectors or electronic absorption.

Presented below is an analysis of the sensitivity of this type of THz source/camera system that demonstrates its ability to image large areas at high repetition rates and thus highlights the substantial advantages of such a source over other existing sources.

For the purposes of this calculation we use parameters close to what are routinely achieved at the Jefferson Lab, namely 135 picocoulomb bunches of electrons at 100 MeV, and 75 MHz repetition rate. The THz radiation output of this source as a function of frequency has been calculated as shown in FIG. 1 attached hereto.

As is shown in FIG. 1, the spectral content depends on the electron bunch length which is an adjustable parameter over the 0.1 to 0.8 ps range. A 0.3 ps full width half maximum (FWHM) operating point and 100 pC is assumed in the following discussion. The total integrated power emitted is 540 W with the spectral intensity peaking above 5 W/cm$^{-1}$. This light is emitted in a cone with an opening angle on the order of 100 mrad. Reflective or transmissive optics of non-absorbing materials may be used to collimate and/or direct this beam to an object under investigation. The assumptions include that the object under study has a fully illuminated area of 1 m$^2$ and is located 2 m from the output of the collection optics and that there are no atmospheric absorption or other losses. The reflectivity of most materials in the THz region has not been well characterized but for purposes of this analysis it is assumed that 30% of the incident power is reflected back into a $2\pi$ steradian solid angle. Thus, the object produces 2.3 e$^{-13}$ W/cm$^{-1}$/mm$^2$/mrad$^2$ for detection. Assuming an emissivity of 0.3 it also produces 10$^{-16}$ W/cm$^{-1}$/mm$^2$/mrad$^2$ of thermal emission.

Figure 2:
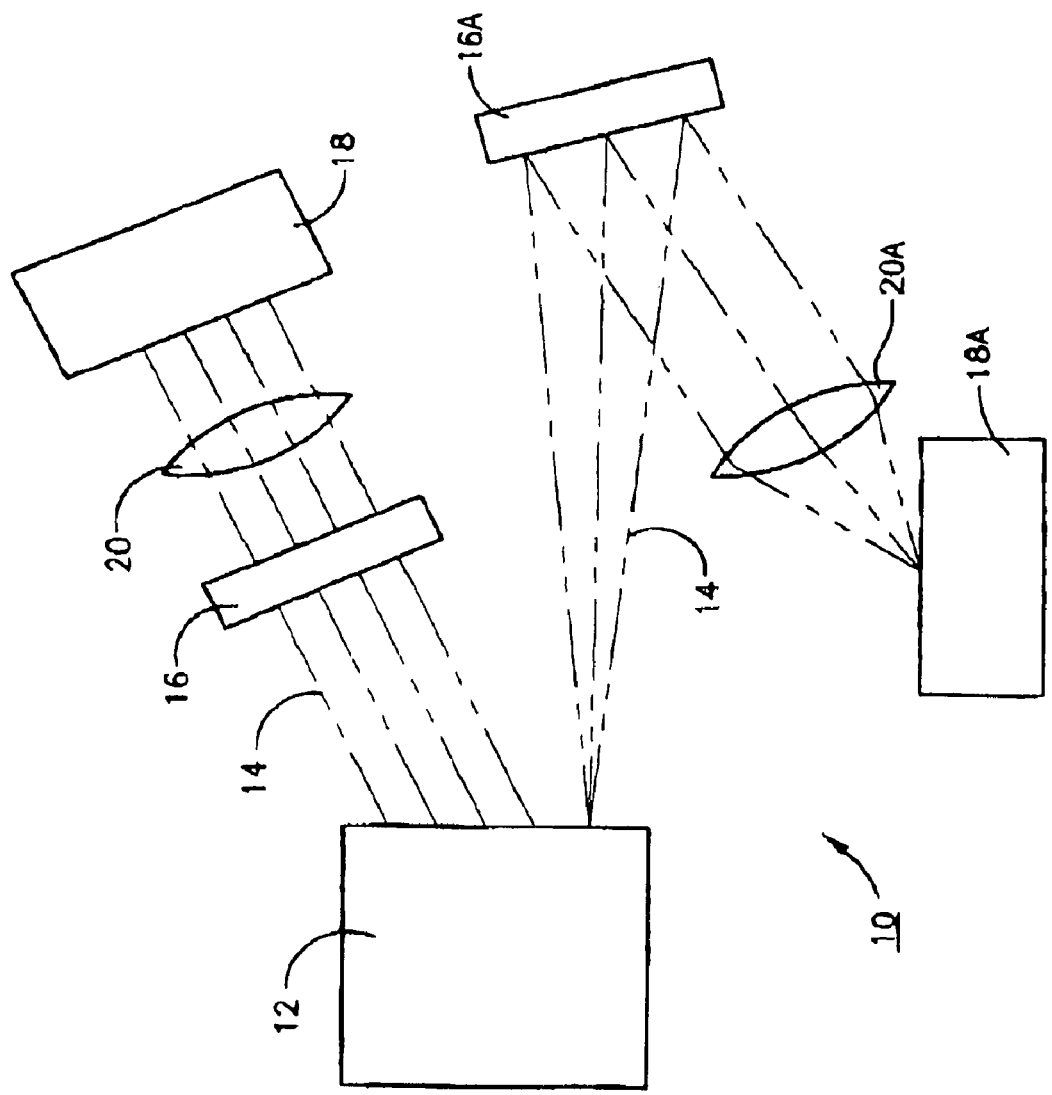
FIG. 2 is a schematic representation of an imaging system suitable for use in the method of the present invention.

As shown in FIG. 2, the imaging system 10 begins with a THz radiation source 12 that produces radiation 14, as described above, that illuminates objects 16 and 16A under study. The detection systems/cameras 18 (for transmitted radiation) and 18A (for reflected radiation) comprise collection lenses 20 and 20A about 10 cm diameter and extending a solid angle 0(1.96 millisteradian. This is applied to THz imaging cameras 18 and 18A or single detector (where the viewing point that the detector sees is scanned). Excellent commercial cameras for this region have Noise Equivalent Powers (NEPs) of 45 nW/Hz$^{1/2}$/pixel (such as the Pyrocam III, available from Spiricon Corp, 2600 North Main Street, Logan, Utah 84341, USA) and a sensitivity of 220 nW/pixeL To improve the sensitivity of the detection relative to electrical noise, the signal is typically chopped. For purposes of this analysis, it is assumed that chopping is at 24 Hz with detection averaged over 1 second. Cameras 18 and 18A include a 124×124 array of 85 micron elements on a 100 micron spacing. To assure that imaging of the 1 m object covers 100% of cameras 18 and 18A each pixel observes 0.65 cm$^2$ and receives 3 e$^{-8}$ W/cm$^{-1}$. Therefore each pixel can detect the scattering providing that the bandwidth is at least 7 cm$^1$. Obviously losses will exist in any system which will reduce this sensitivity. It is also necessary to be able to resolve the object. At 1 mm wavelength the resolution for this 10 cm optic is 2 cm at objects 16 and 16A.

Custom detectors based on antenna coupled bolometric arrays or resonant tunneling diodes have sensitivities that are 1000 times higher than the Pyrocam III, and allow true video-frame rate sampling at higher spectral resolution are also available and can be used in the successful practice of the present invention.

There has thus been described a THz imaging method and system capable of obtaining real time images using transmitted or reflected THz light with all of the attendant advantages that such a system provides in terms of detection and materials characterization.

As the invention has been described, it will be apparent to those skilled in the art that the same may be varied in many ways without departing from the spirit and scope of the invention. Any and all such modifications are intended to be included within the scope of the appended claims.

What is claimed is:

1. A THz real time imaging system comprising:
    A) a compact high power THz light source having an output greater than 1 watt for illuminating an object; said light source comprising:
        1) a mechanism for introducing THz radiation in the form of a beam of photon pulses comprised of a series of photon bunches; and
        2) a cavity defined by at least one pair of facing optical mirrors that produces reflected photon pulses when the THz radiation is introduced into the cavity, the cavity providing synchronously reflected photon pulses, that encounter an electron bunch or another photon pulse traveling in the same direction and energy is transmitted from the electron bunch or the other photon pulse resulting in an increase in the energy of the reflected photon pulse;
    B) a collection lens; and
    C) a camera for making a picture of the object under study, whereby said picture is made almost instantaneously.

2. The THz real time imaging system of claim 1:
    wherein said video pictures are made almost instantaneously of the object under study.

3. The THz real time imaging system of claim 1:
    wherein the speed of acquisition of said picture occurs at a rate of at least thirty frames per second full field.

4. The real-time imaging system of claim 3 wherein said camera includes an array having a plurality of pixels.

5. The real-time imaging system of claim 3 wherein said camera has a Noise Equivalent Power of approximately 45 nW/Hz1/2/pixels or better and a sensitivity of 220 nW/pixels or better.

* * * * *